United States Patent [19]
Johnson et al.

[11] Patent Number: 5,445,640
[45] Date of Patent: Aug. 29, 1995

[54] TIBIAL RESECTOR GUIDE

[75] Inventors: Todd S. Johnson; Richard A. Lane, both of Fort Wayne, Ind.; Thomas D. Petersen, San Diego, Calif.; Chuck Nichols; John R. Howard, both of Addison, Ill.

[73] Assignee: Zimmer, Inc., Warsaw, Ind.

[21] Appl. No.: 30,954

[22] Filed: Mar. 12, 1993

Related U.S. Application Data

[63] Continuation of Ser. No. 805,696, Dec. 10, 1991, abandoned.

[51] Int. Cl.⁶ .................................. A61F 5/00
[52] U.S. Cl. ............................. 606/86; 606/87
[58] Field of Search ............. 606/62, 86, 87, 88, 606/89, 90, 79, 80, 96, 97, 98

[56] References Cited

U.S. PATENT DOCUMENTS

| | | | |
|---|---|---|---|
| 2,371,519 | 3/1945 | Haynes | 128/84 |
| 4,457,307 | 7/1984 | Stillwell | 128/317 |
| 4,467,801 | 8/1984 | Whiteside | 128/303 R |
| 4,501,266 | 2/1985 | McDaniel | 128/69 |
| 4,524,766 | 6/1985 | Petersen | 128/92 |
| 4,703,751 | 11/1987 | Pohl | 606/62 |
| 4,736,737 | 4/1988 | Fargie et al. | 128/92 |
| 4,738,253 | 4/1988 | Buechel | 606/96 |
| 4,759,350 | 7/1988 | Dunn | 606/82 |
| 4,773,407 | 9/1988 | Peterson | 128/92 |
| 4,841,975 | 6/1989 | Woolson | 606/96 |
| 4,952,213 | 8/1990 | Bowman | 606/62 |
| 5,002,547 | 3/1991 | Poggie et al. | 608/88 |
| 5,020,519 | 6/1991 | Hayes et al. | 128/69 |
| 5,053,039 | 10/1991 | Hofmann | 606/86 |

FOREIGN PATENT DOCUMENTS

0415837A2  3/1991  European Pat. Off.

*Primary Examiner*—Michael A. Brown
*Attorney, Agent, or Firm*—Todd A. Dawson

[57] ABSTRACT

A tibial resector guide having an angularly adjustable head controlled by a thumb actuated slide mechanism. The head may be positioned in a plurality of predetermined angular orientations in the anterior-posterior plane. The cutting head guide includes angled side walls which permit the guide to have a narrow aperture yet allow the saw blade to completely pass through the tibia. Further, the tibial resector of this invention includes a telescoping rod and a length adjustment mechanism adjacent the head for providing small height adjustments for positioning the head. The length adjustment member includes an enlarged thumb wheel to ease operation. A pinning platform is connected to the adjustment member such that it is shiftable with the adjustment member relative to the guide head. The pinning platform permits the surgeon to pin the upper end of the instrument to the patient's leg preventing movement of the instrument during resection. After pinning, the head may be further adjusted in height by rotating the adjustment member. The instrument further includes a sliding ankle adjustment to provide proper alignment of the guide with the tibia and femur.

5 Claims, 4 Drawing Sheets

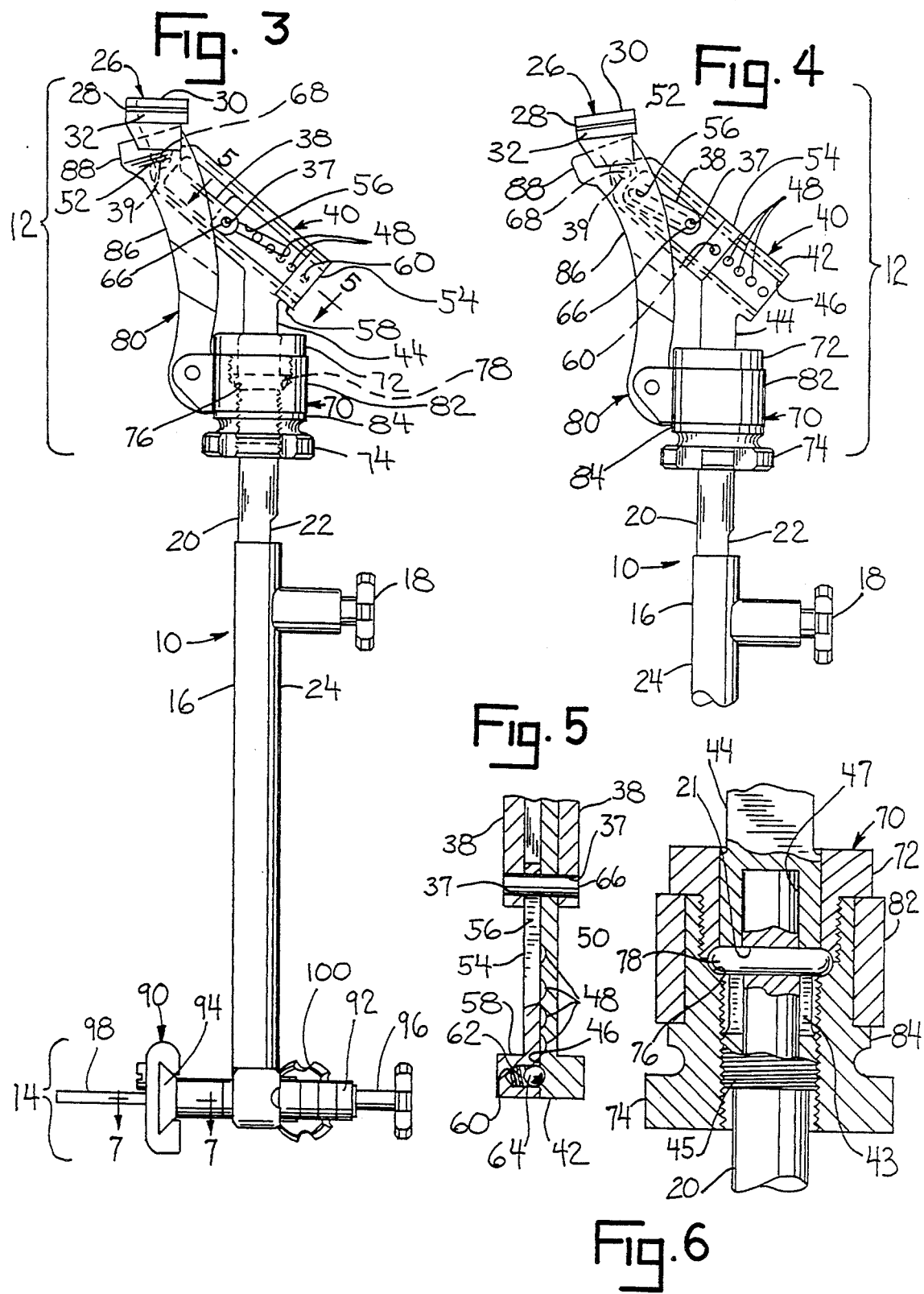

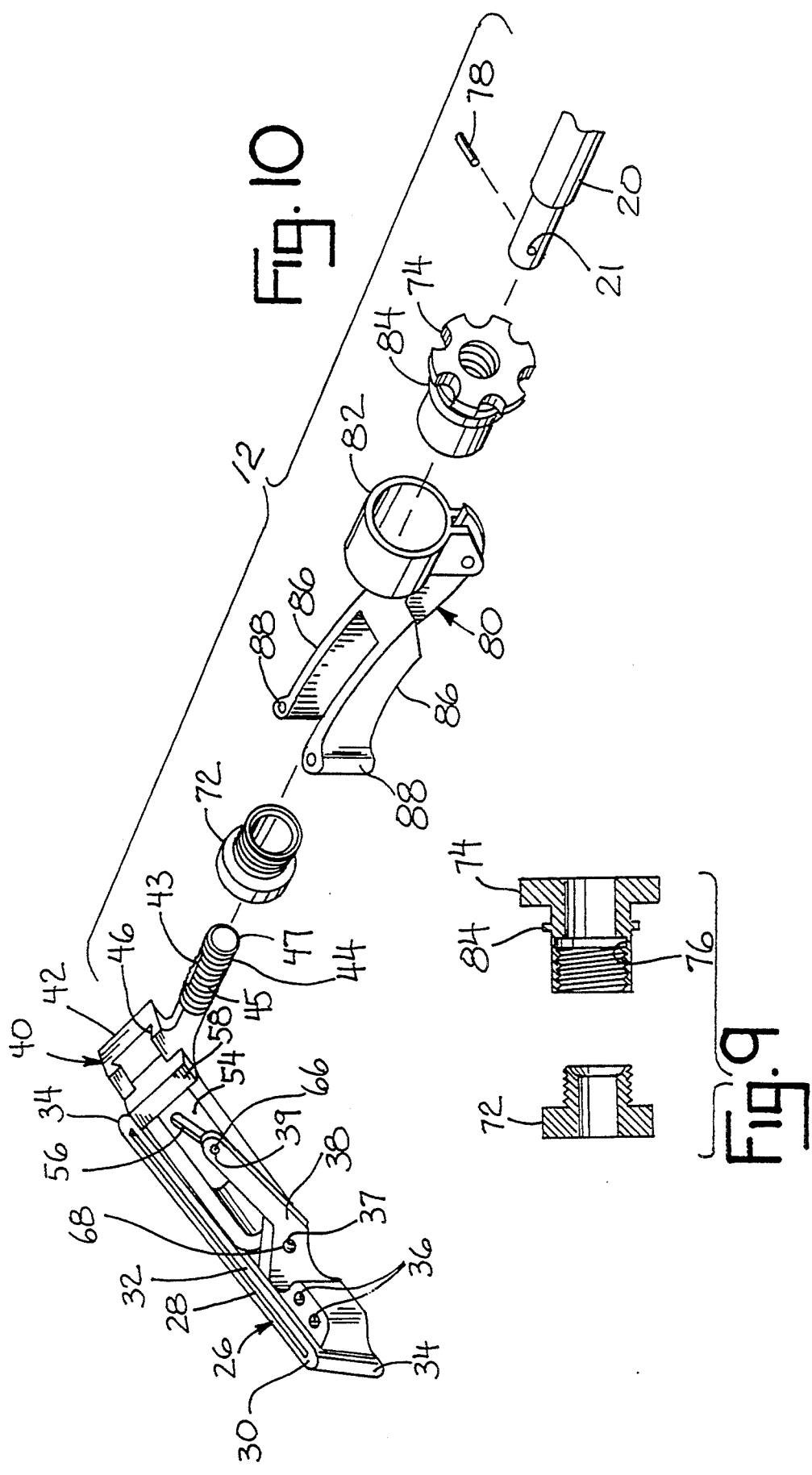

TIBIAL RESECTOR GUIDE

This is a continuation of application Ser. No. 07/805,696, filed Dec. 10, 1991, now abandoned.

BACKGROUND OF THE INVENTION

This invention relates to resector guides as used in orthopaedic surgery and has specific relevance to a tibial resector guide having a guide head which may be selectively angled in an anterior-posterior plane.

BACKGROUND OF THE INVENTION

During the surgical procedure to implant a knee prosthesis, the proximal end of the tibia must be cut to accommodate the tibial implant. Proper fit and function of the knee prosthesis will depend in large part on the accuracy of the tibial cut. Therefore, it is not uncommon for a surgeon to place a cutting guide in close proximity with the proximal end of the tibia. Prior art cutting guides typically include a head which accommodates the bone saw blade. The surgeon passes the saw blade along the guide head to resect a proximal portion of the tibia. Tibial resector guides, in general, are not new. A number of such guides have been developed and patented throughout the years.

The Woolson U.S. Pat. No. 4,841,975 discloses a tibial resector guide having a telescoping rod carrying a cutting head at its upper end. The cutting guide is adjustable relative to the telescoping rod by a pair of oppositely positioned thumb screws. The guide may be aligned with the mechanical axis of the joint by use of a slidable plate.

Poggie et al., U.S. Pat. No. 5,002,547 and Petersen U.S. Pat. No. 4,524,766 disclose tibial resector guides wherein the cutting guides are fixed to a telescoping rod.

Dunn et al., U.S. Pat. No. 4,759,350, discloses a tibial resector guide having a fixed head carried by a telescoping rod. A separate pinning strap is carried by the rod adjacent the head. The strap 106 is fixed to the telescoping rod.

Fargie et al., U.S. Pat. No. 4,736,737, discloses a tibial resector head connected to an intramedullary rod and shiftable in a longitudinal direction only. Angular adjustment is not provided.

Petersen, U.S. Pat. No. 4,773,407, discloses an instrument for guiding the resection of a distal femur having a head which is pivotally carried by a guide rod. The pivotal head is for the purpose of providing alignment and not posterior slope. The guide rod carries a rotating rod having holes therethrough for accommodating a securement pin.

SUMMARY OF THE INVENTION

This invention provides for a tibial resector guide having an angularly adjustable head controlled by a thumb actuated slide mechanism. The head may be positioned in a plurality of predetermined angular orientations in the anterior-posterior plane. The head guide includes angled side walls which permit the guide to have a narrow anterior aperture yet allow the saw blade to completely pass through the tibia. Further, the tibial resector of this invention includes a length adjustment mechanism on the head for providing small height adjustments for positioning the cutting guide. The length adjustment member includes an enlarged thumb wheel for ease of operation. A pinning fork is pivotally connected to the adjustment member and extends upwardly adjacent the cutting guide. The pinning fork permits the surgeon to pin the upper end of the instrument to the patient's leg preventing movement of the instrument during resection. After pinning, the cutting guide may be further adjusted in height by rotating the length mechanism. The resector guide further includes a sliding ankle adjustment to provide proper alignment of the guide with the mechanical axis of the joint.

Accordingly, it is an object of the invention to provide for a novel tibial resector guide.

Another object of the invention is to provide an adjustable resector guide head.

Another object of the invention is to provide for a tibial resector having a height adjustment member for providing small increments in height.

Still another object of this invention is to provide for a tibial resector guide having a narrow aperture cutting guide with outwardly inclined side walls to provide an enlarged cutting area.

BRIEF DESCRIPTION OF THE DRAWINGS

FIG. 3 is a side elevational view of the tibial resector of the invention.

FIG. 4 is a fragmented side elevational view of the invention illustrating the head in its fully angled position relative to the shaft.

FIG. 5 is a fragmented sectional view taken along line 5—5 of FIG. 3.

FIG. 6 is a fragmented Sectional view taken along line 6—6 of FIG. 2.

FIG. 9 is an exploded view of the length adjustment mechanism of the invention.

FIG. 10 is an exploded view of the head of the tibial resector guide of the invention.

DESCRIPTION OF THE PREFERRED EMBODIMENT

Figures 1, 2:
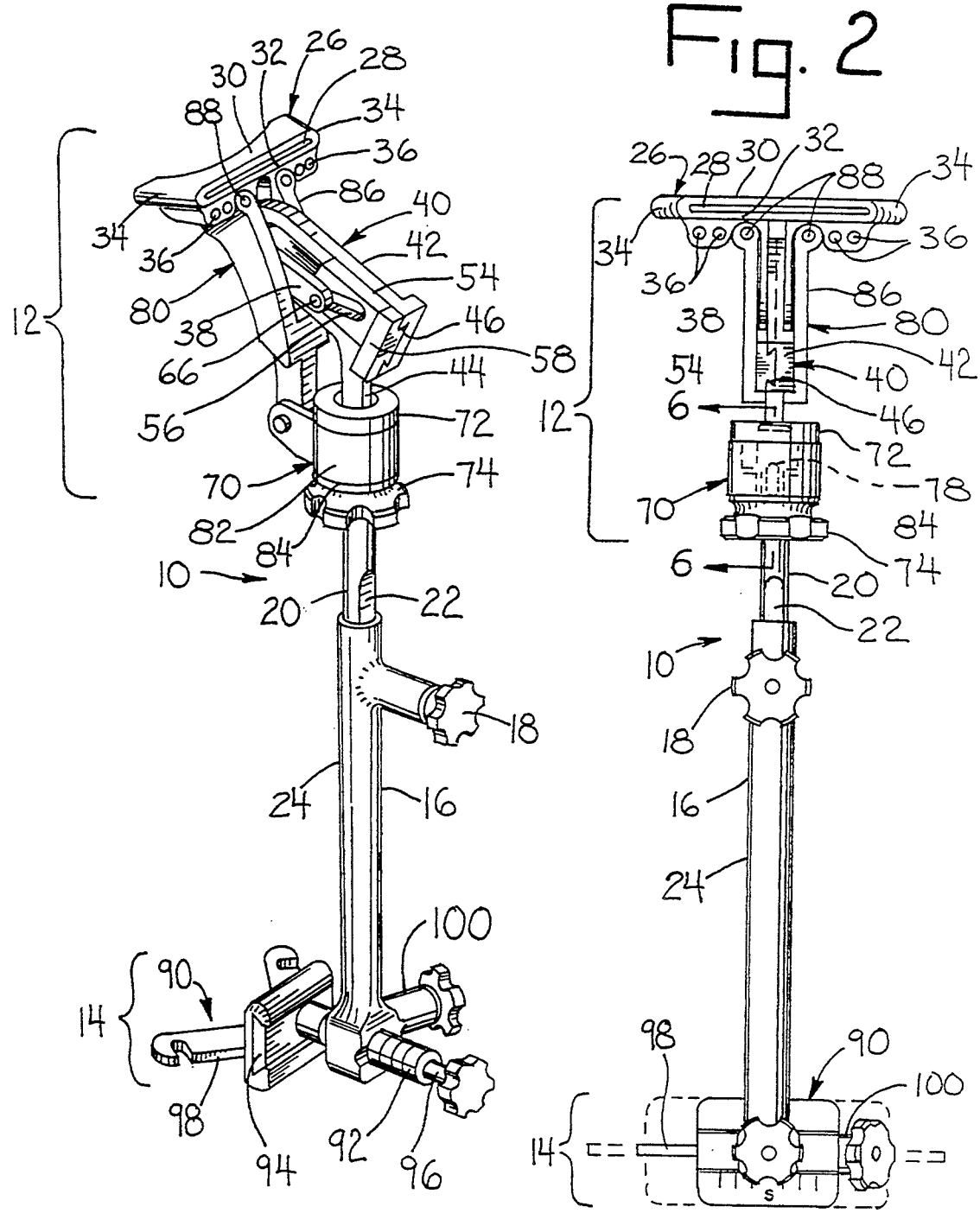
FIG. 1 is a perspective view of the tibial resector of this invention.
FIG. 2 is a rear elevational view of the tibial resector of this invention.

The preferred embodiment herein disclosed is not intended to be exhaustive or to limit the invention to the precise form disclosed. Rather, it is chosen and described in order to best explain the invention so that others skilled in the art can utilize its teachings.

Referring now to the drawings, tibial resector guide 10 includes a head 12 and an ankle adjustment mechanism 14 interconnected by a telescoping rod 16. Rod 16 is adjustable in length and is maintained at a fixed position by turning thumb wheel 18 to cause a screw (not shown) to engage the inner rod 20. Inner rod 20 includes a flattened side 22 for contact with the screw (not shown) to prevent rotation of inner rod 20 relative to outer tube 24. The distal tip of inner rod 20 includes a transverse bore 21.

Head 12 includes a cutting guide 26 having upper and lower walls 30, 32 and side walls 34 defining a slot 28 for accommodating the blade of a bone saw (not shown). An arcuate recess is formed in the posterior side of upper and lower walls 30, 32 for accommodating the proximal portion of a patient's lower leg adjacent the knee joint. Side walls 34 of the guide diverge from the anterior side toward the posterior side of the upper and lower walls such that the opening of slot 28 on the anterior side of the guide is longitudinally smaller than the opening of the slot on the posterior side of guide 26. This feature permits the use of a full stroke cutting guide 26 allowing the entire tibia to be cut through in one pass within the confined area of the surgical site. A plurality of pinning apertures 36 are provided extending from the bottom surface of the guide 26. Pinning apertures 36 accommodate a fixation pin during surgery to secure guide 10 against movement during resection. A pair of legs 38 extend at an angle from lower wall 32 of guide 26 and each include through bores 37, 39.

Figure 8:
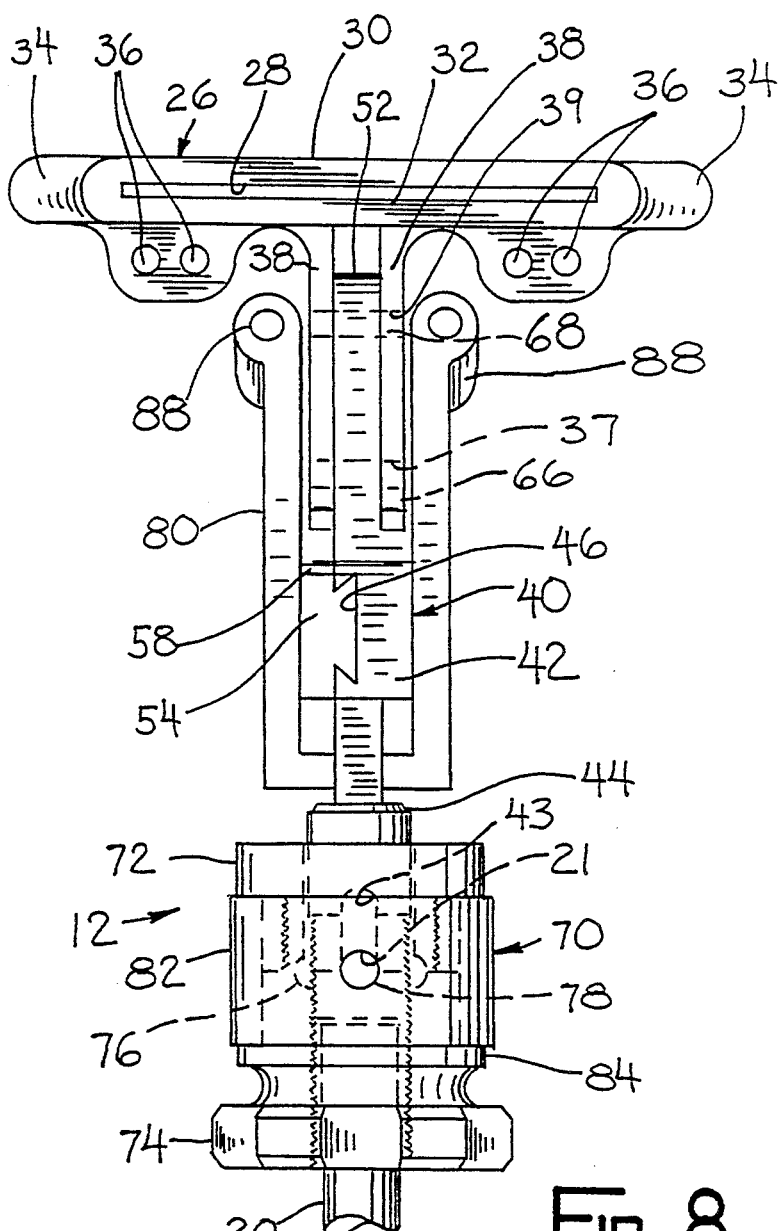
FIG. 8 is a fragmented elevational view of the head, pinning fork and adjustment mechanism with the pinning fork fully spaced from the guide head.
Figure 7:
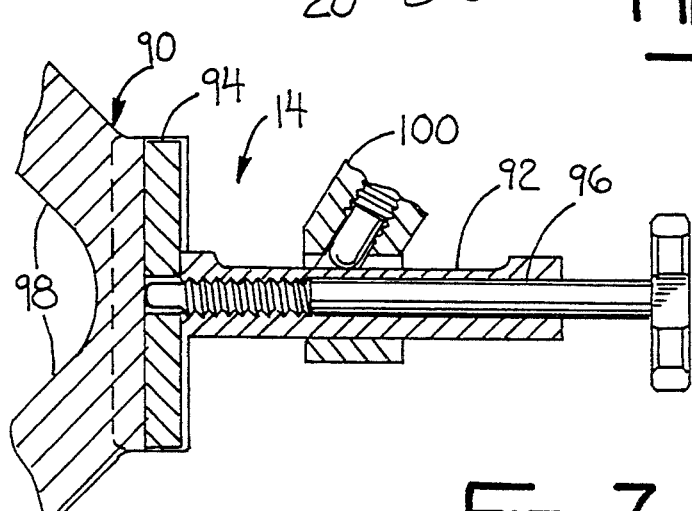
FIG. 7 is a fragmented sectional view taken along line 7—7 of FIG. 3.

Head 12 further includes a posterior slope adjustment mechanism 40 for selectively angling the cutting guide 26 relative to rod 16. Slope adjustment mechanism 40 includes a fixed body 42 having a downwardly extending leg 44. The distal portion of leg 44 includes screw threads 45. A longitudinally aligned slot 43 is formed through leg 44 and threads 43. A central blind bore 47 extends inwardly into leg 44. Body 42 is longitudinal in dimension and has a dovetail slot 46 formed in one side wall thereof. A plurality of indentions 48 are formed in the inner wall of the dovetail slot. A slot 50 is formed through body 42 in communication with dovetail slot 46. Body 42 terminates in a protrusion 52 having a bore therethrough. Slope adjustment mechanism 48 further includes a slide 54 accommodated within dovetail slot 46 and slidable between a fully retracted position of FIGS. 1, 2, 3, and 8 and the fully extended position of FIG. 4. Slide 54 includes a slot 56 positioned at an angle with the slide as illustrated. A thumb bar 58 extends outwardly from slide 54 to provide access to the user. As best illustrated in FIG. 5, slide 54 includes a blind bore 60 which carries a helical spring 62 and a ball stop 64. As illustrated in FIG. 5, spring 62 urges ball stop against the inner wall of dovetail slot 46. As slide 54 is shifted between its extremes, ball stop 64 seats within indentations 48 to impart a positive snap feel to the slide.

Guide 26 is pivotally connected to the slope adjustment mechanism by a screw 68 press threaded through a pair of aligned openings in legs 38 of guide 26 and the bore of knob 52. A screw 66 interconnects the distal ends of legs 38 and is accommodated within slot 56 of slide 54 and slot 50 of fixed body 42. As slide 54 is shifted between its extreme positions, screw 66 rides within the angled slot 56 causing the cutting guide 26 to pivot about pin 68 to thereby vary the angle of inclination of the slot 28 relative to the fixed body 42.

Head 12 also includes a length adjustment mechanism 70 which provides small adjustments in the overall length of the tibia resector guide 10. Length adjustment mechanism 70 (hereinafter referred to as LAM 70) includes a cap 72 having a lower depending shaft with external threads an a central bore dimensioned to loosely accommodate leg 44. LAM 70 further includes a cylindrical body 74 having a central longitudinal bore stepped in diameter to threadibly accommodate cap 72 at one end and leg 44 at the opposite end. As cylindrical body 74 rotates relative to leg 44, body 74 travels along threads 45 of leg 44. The lower depending shaft of cap 72 and the central bore of cylindrical body 74 are formed such that when cap 72 is fully screwed into cylindrical body, a ring shaped cavity 76 is formed therebetween. The distal end of inner rod 20 is slidably positioned within the central blind bore 47 of leg 44. A pin 78 is inserted into bore 21 of rod 20 and extends outwardly therefrom for slidable accommodation within slot 43 of leg 44.

Finally, head 12 includes a pinning fork 80 pivotally connected to a collar 82 loosely carried by cylindrical body 74 such that the collar remains rotationally stationary as body 74 rotates. Pinning fork 80 is slightly arcuate in its side view and includes a pair of arms 86 each of which terminate in a pinning tube 88. Arms 86 are positioned laterally adjacent legs 38 of cutting guide 26. The distal ends of arms 86 are accommodated within recesses formed in the underneath side of lower wall 32 as shown.

Ankle adjustment mechanism 14 includes an ankle contacting member 90 slidably carried by the foot 94 of a shaft 92. A threaded rod 96 is accommodated within shaft 92 and causes a restrictive interference between member 90 and foot 94 when rod 96 is rotatably extended toward member 90. Member 90 includes a pair of legs 98 spaced from one another for straddling the patients ankle. Shaft 92 is carried by outer tube 24 or telescoping rod 16 and is selectively lockable in position relative to tube 24 by a interfering locking device 100.

In use, tibial resector guide 10 is positioned adjacent the patient's lower leg such that ankle adjustment mechanism 14 is adjacent the patient's ankle with legs 98 straddling the ankle. Thumb wheel 18 is rotated to release inner rod 16 and the head 12 is positioned in such that cutting guide 26 is in the approximate position for the tibial cut predetermined by the surgeon. The ankle adjustment mechanism 14 is adjusted so as to align device 10 with the mechanical axis of the knee joint for proper installation of the tibial component. Telescoping rod 16 is positioned in parallel with the tibia. The particular reasons for adjusting the ankle adjusting mechanism 14 are well known in the industry and need not be discussed here. After mechanism 14 has been appropriately adjusted and the cutting guide is at least approximately in position relative to the desired cut line, the surgeon may insert a stabilizing pin through each pinning tube 88 of the pinning fork and into the tibia.

To precisely align slot 28 with the intended cut line, the surgeon rotates cylindrical body 74 of LAM 70. As mentioned previously, leach longitudinal end of pin 78 is seated within the ring-like cavity formed between cap 72 and body 74 of LAM 70 with the remaining portion of the pin carried within bore 21 of inner rod 20. Pin 78 acts as an anchor to longitudinally fix the combination of cylindrical body 74 and cap 72 to inner rod 20. Therefore, with leg 44 threadibly accommodated within cylindrical body 74, rotation of cylindrical body 74 causes leg 44 to travel longitudinally within the cylindrical body 74. Pin 78 accommodated within slot 43 of leg 44 defines the longitudinal extremes the leg's shifting relative to rod 20. A longitudinal shift in leg 44 shifts cutting guide 26 relative to rod 20 thereby changing the overall length of the tibial resector guide 10.

Therefore, the telescoping rod 16 may be used by the surgeon to set the cutting guide in the approximate location for the cut. The length adjustment mechanism may then be used to precisely align the cutting guide 26 with the desired cut line. This precise alignment is possible due to the interplay of the cylindrical body 74, pin 78 and leg 44. The threaded adjustment of the resector length provides for infinite and precise adjustment of the cutting guide 26. In practice, leg 44 may include indicia which may be referenced against the top of cap 72 to provide visual indication of the amount of movement of the leg relative to rod 20. Preferably, the indicia will be spaced in 2 mm increments.

The anterior-posterior (A-P) angle of the cutting guide 26 may be altered relative to telescoping rod 16 by adjustment of the slope adjustment mechanism 40. To vary the A-P slope of the cutting guide 26, the surgeon shifts slide 54 relative to fixed body 42 within the dovetail groove 46. As slide 54 is shifted within the groove, screw 66 (accommodated within the angled slot 56 of slide 54) follows slot 54 which translates into a vertical motion within slot 50 of fixed body 42. This vertical movement of screw 66 connected to the distal ends of legs 38 causes the cutting guide 26 to pivot about pivot pin 68 thereby causing a change in the A-P slope of the cutting guide 26 and more importantly, slot 28. As slide 54 is shifted within dovetail groove 46, ball stop 64 seats within each indentation 48 to impart a positive snap feel to the slide. Each indentation corresponds to a particular angular setting of the cutting head as is indicated by indicia on the upper surface of the fixed body as shown in the figures. In the preferred embodiment the indentations correlate to 0, 3, 5, 7 and 10 degrees of A-P slope relative to the telescoping rod 16. Since the angles of slope adjustment mechanism 40 are referenced from the telescoping rod it is imperative that the rod be parallel the tibia.

Once head 12 has been properly adjusted and the cutting guide 26 is in contact with the proximal portion of the tibia, the surgeon may pin the cutting guide 26 in place by placing pins through pinning apertures 36. A cutting blade (not shown) from a powered cutting instrument is inserted into slot 28 and the instrument activated to saw through the tibia at the cut line. As mentioned, the environment of a typical total knee replacement procedure is somewhat cramped with limited space available. Therefore, the cutting guide 26 of the invention is formed with angled side walls 34 as illustrated. The angled side walls present a narrow face of the cutting guide to the surgeon, thus taking up less space, yet provide a full cutting aperture adjacent the tibia. To complete a full cut, the surgeon must follow the angled side walls of the cutting guide 26.

It should be understood that after the surgeon selects the appropriate A-P angle, the position of the cutting guide 26 may need to be longitudinally altered by LAM 70.

It should be understood that the invention is not to be limited to the precise form disclosed but may be modified within the scope of the appended claims.

We claim:

1. An adjustable head for an orthopaedic resector guide comprising an elongated fixed body, a slide carried by said elongated fixed body and a cutting guide pivotally connected to said fixed body and operatively associated with said slide, said slide being shiftable along said fixed body between first and second longitudinal positions relative to said fixed body, said cutting guide engaged with said slide so as to pivot relative to said fixed body as said slide is shifted between its first and second longitudinal positions.

2. The adjustable head of claim 1 wherein said fixed body includes a plurality of recesses and said slide carries shiftable stop member for progressive engagement within each such recess as said slide is shifted between its first and second positions, said stop member and said recesses constituting detent means for imparting a positive snap feel to said slide as it is shifted relative to said fixed body.

3. The adjustable head of claim 1 wherein said slide rides within a longitudinal groove of said fixed body.

4. A cutting head for a resector guide for use in orthopaedic surgery, said head comprising integral anterior side and posterior side walls and end walls, a slot formed through said posterior and anterior side walls for accommodating a surgical blade therein, said posterior side wall being longer than said anterior side wall such that said end walls converge toward said anterior side wall, the opening of said slot being longer at said posterior side wall than at said anterior side wall.

5. An adjustable head for an orthopaedic resector guide comprising a fixed body, a slide carried by said body, and a cutting guide pivotally connected to said fixed body and operatively associated with said slide, said slide being shiftable relative to said fixed body between first and second longitudinal positions on said fixed body, said cutting guide engaged with said slide so as to pivot relative to said fixed body as said slide is shifted between its first and second positions, wherein said fixed body includes a plurality of recesses and said slide carries a shiftable stop member for progressive engagement within each such recess as said slide is shifted between its first and second positions, said stop member and said recesses constituting detent means for imparting a positive snap feel to said slide as it is shifted relative to said fixed body.

* * * * *